United States Patent
Sperrhake et al.

(10) Patent No.: US 12,053,267 B2
(45) Date of Patent: Aug. 6, 2024

(54) METHOD AND DEVICE FOR THE NON-CONTACT DETERMINATION OF COLOR AND INTENSITY VARIATIONS OVER TIME IN OBJECTS

(71) Applicants: FRIEDRICH-SCHILLER-UNIVERSITÄT JENA, Jena (DE); UNIVERSITÄTSKLINIKUM JENA, Jena (DE); OTTO-VON-GUERICKE-UNIVERSITÄT MAGDEBURG, Magdeburg (DE); FRAUNHOFER-GESELLSCHAFT ZUR FÖRDERUNG DER ANGEWANDTEN FORSCHUNG E.V., Munich (DE)

(72) Inventors: Jan Sperrhake, Jena (DE); Thomas Pertsch, Hermsdorf (DE); Maria Nisser, Jena (DE); Michal Rapczynski, Magdeburg (DE); Ayoub Al-Hamadi, Magdeburg (DE); Chen Zhang, Ilmenau (DE); Gunther Notni, Jena (DE)

(73) Assignees: FRIEDRICH-SCHILLER-UNIVERSITÄT JENA, Jena (DE); UNIVERSITÄTSKLINIKUM JENA, Jena (DE); OTTO-VON-GUERICKE-UNIVERSITÄT MAGDEBURG, Magdeburg (DE); FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 240 days.

(21) Appl. No.: 17/779,972

(22) PCT Filed: Nov. 26, 2020

(86) PCT No.: PCT/EP2020/083497
§ 371 (c)(1),
(2) Date: May 25, 2022

(87) PCT Pub. No.: WO2021/110531
PCT Pub. Date: Jun. 10, 2021

(65) Prior Publication Data
US 2022/0409078 A1    Dec. 29, 2022

(30) Foreign Application Priority Data

Dec. 2, 2019   (DE) .................. 10 2019 132 708.3
Mar. 24, 2020  (DE) .................. 10 2020 108 064.6

(51) Int. Cl.
*A61B 5/024*   (2006.01)
*A61B 5/00*    (2006.01)
*G01C 11/18*   (2006.01)

(52) U.S. Cl.
CPC ........ *A61B 5/02427* (2013.01); *A61B 5/0073* (2013.01); *A61B 5/0077* (2013.01); *G01C 11/18* (2013.01)

(58) Field of Classification Search
CPC . A61B 5/02427; A61B 5/0073; A61B 5/0077; A61B 5/02416; A61B 5/14551; G01C 11/18
See application file for complete search history.

(56) References Cited

U.S. PATENT DOCUMENTS 9,750,420 B1    9/2017  Agrawal et al.
10,936,890 B2 * 3/2021  Okayasu .............. G06V 20/593
(Continued)

FOREIGN PATENT DOCUMENTS

EP           3838128 A1 *  6/2021  ......... A61B 5/02416
WO   WO-2019157190 A1 *  8/2019  ........... A61B 5/0077

OTHER PUBLICATIONS

Junger, Stephan, et al., "Multipectral CMOS sensors with on-chip nanostructures for wavelength monitoring of LED devices," *Proceedings of SPIE*, vol. 8641, 6 pages (2013).
(Continued)

*Primary Examiner* — Michael Lee
(74) *Attorney, Agent, or Firm* — Christensen, Fonder, Dardi & Herbert PLLC (57) ABSTRACT

A method and a device for non-contact determination of temporal color and/or intensity variations in objects in a scene. Monoscopic overview images of the scene are detected with first and second overview cameras from two different viewing directions, and calculated to form a stereoscopic overview map. A two-dimensional detail image is detected by a detail camera from a third viewing direction and is projected on the overview map. Measurement sur-
(Continued)

faces in the scene are selected based on criteria which are predetermined depending on parameters on which conclusions are to be drawn from the color variations and/or intensity variations. Light emitted by the measurement surfaces is detected in a spatially-resolved and wavelength-resolved manner in a continuously-captured series of measurement images in a predetermined spectral range. The measurement surfaces are analyzed in the measurement images with respect to temporal variation of the intensity and/or color of the light, and the results displayed.

19 Claims, 4 Drawing Sheets

(56) References Cited

U.S. PATENT DOCUMENTS

| | | | |
|---|---|---|---|
| 11,903,723 B2* | 2/2024 | Barclay | A61B 5/7475 |
| 2015/0190077 A1* | 7/2015 | Kim | A61B 5/14551 |
| | | | 600/323 |
| 2015/0379362 A1 | 12/2015 | Calmes et al. | |
| 2016/0155006 A1 | 6/2016 | Makkapati et al. | |
| 2016/0278644 A1* | 9/2016 | He | A61B 5/7275 |
| 2018/0276448 A1* | 9/2018 | Kim | A61B 5/7221 |
| 2019/0213312 A1* | 7/2019 | Tussy | G06Q 20/3276 |
| 2019/0246920 A1* | 8/2019 | Zhang | A61B 5/318 |
| 2023/0027982 A1* | 1/2023 | Kellner | A61B 5/4824 |
| 2024/0085924 A1* | 3/2024 | Cristache | G05D 1/027 |

OTHER PUBLICATIONS

Heist, Stefan, et al., "GOBO projection for 3D measurements at highest frame rates: a performance analysis," *Light: Science & Applications*, 7:71, 13 pages (2018).

Blanik, Nikolai, et al., "Hybrid optical imaging technology for long-term remote monitoring of skin perfusion and temperature behavior," *Journal of Biomedical Optics*, 19(1), 12 pages (Jan. 2014).

Wieringa, F.P., et al., Remote Non-invasive Stereoscopic Imaging of Blood Vessels: First In-vivo Results of a New Multispectral Contrast Enhancement Technology, *Annals of Biomedical Engineering*, Vo. 34, No. 12. pp. 1870-1878 (Dec. 2006).

* cited by examiner

METHOD AND DEVICE FOR THE NON-CONTACT DETERMINATION OF COLOR AND INTENSITY VARIATIONS OVER TIME IN OBJECTS

PRIORITY CLAIM

The present application is a National Phase entry of PCT Application No. PCT/EP2020/083497, filed Nov. 26, 2020, which claims priority to German Patent Application No. 10 2019 132 708.3, filed Dec. 2, 2019, and German Patent Application No. 10 2020 108 064.6, filed Mar. 24, 2020, the disclosures of which are hereby incorporated by reference herein in their entirety.

FIELD OF THE INVENTION

The invention is directed to a method and a device for the contact-free determination of temporal color variations and intensity variations in objects in a scene, for example, in sports centers or hospitals but also in plants. A range of methods is known in the prior art for monitoring the health status of athletes or for performance diagnostics of athletes. But these methods rely predominantly on contact with the persons. The variations in color and intensity relate to light of determined wavelengths which is either actively emitted by the object itself, for example, an LED, or which is partially absorbed or attenuated by the object when illuminated and is therefore not reflected in its entirety. In the literal sense, the term "color variations" generally refers to changes in wavelength, i.e., for example, the shifting of a reflection maximum or transmission maximum within narrow wavelength ranges. The term "intensity variations" generally refers to variations in the maximum reflection or transmission at a constant wavelength. In the domain of sports medicine applications, however, "color variations" is understood as also meaning intensity variations because the latter seem to bring about a color variation subjectively and merely apparently by a change in brightness, which is actually not the case for an individual color or wavelength but only for the overall impression produced by the mixture of all of the colors or wavelengths; that is, when the intensity of a centroid color changes, an observer receives a different overall impression of color on the whole in the color mixture of the individual wavelengths. An example of this is jaundice in humans, particularly newborns: the higher concentration of bilirubin in the blood leads to a strengthened reflection in the wavelength range between 420 nm and 450 nm and, therefore, to the color perception of the skin as appreciably more yellow than in healthy humans.

DESCRIPTION OF THE PRIOR ART

In order to carry out performance diagnostics on athletes, for example, an electrocardiogram (EKG) of a person to be examined is used to determine the heart rate and heart rate variability, and the method of photoplethysmography (PPG) is used to determine the oxygen saturation. Both methods are contact-based but represent the gold standard of methods owing to their high reliability, objectivity and validity. Their great drawback consists, for one, in that they are contact-based methods, i.e., always only one person can be observed at any one time and, moreover, specially trained technicians are indispensable for exact attachment and application of the electrodes which are needed for the measurement. For example, the skin must be prepared by disinfecting and possibly also shaving. Knowledge of anatomy is required for placement of the electrodes. Moreover, a considerable expenditure of time is required to ensure the comparability of the acquired data. A further disadvantage arises from the necessity for contact-based electrodes which must be applied directly to the skin. Therefore, measurement of the person in question must be carried out in enclosed surroundings to protect privacy. EKG and PPG can be coupled by means of multi-sensor systems and measured simultaneously, but such systems are always assigned to only one individual person.

Contact-based systems such as EKGs and PPGs are also used to monitor the health status of patients in a hospital. These contact-based methods are disadvantageous especially in hospitals, where it would be desirable to monitor a plurality of persons simultaneously, because a plurality of systems would have to be available at the same time and operated in parallel to cover a plurality of persons. The acquisition costs are correspondingly high.

On the other hand, non-contact measurement methods are also known in the art; however, they are not used to detect the performance condition or health status of persons. For example, soils and crops are analyzed when observing the Earth from the air or by satellite. Conventional spectrometers which reproduce an image broken down into many wavelengths are used for this purpose. The evaluation of such data entails a particularly high expenditure especially when special spectral characteristics are involved which serve, for example, as indicators for the condition of, or impact on, forests or arable soils. A breakdown according to depth information which makes it possible, for example, to detect whether the forest soil or the tree tops are being measured is not provided in this procedure.

It has turned out that certain vital parameters such as pulse and blood oxygen level can also be measured without contact. These parameters can be determined based on slight variations in color and intensity in the skin which result from the reflection and absorption of determined wavelengths of the hemoglobin in the blood and the periodically fluctuating level thereof in vessels at various locations on the skin.

However, the temporal analysis of color fluctuations has thus far been used chiefly for characterizing the stability of light emitting diodes. Nanooptical filters, as they are called, which can filter light of determined wavelengths or wavelength ranges based on specific interaction mechanisms are used for this purpose. Such nanooptical elements are described, for example, in an article by S. Junger, et al., "Multispectral CMOS sensors with on-chip nanostructures for wavelength monitoring of LED devices", published in *Proceedings SPIE* (8641), page 86411B (2013). The nanooptical filters are placed in front of the camera for adapting in a simple manner to different wavelengths through exchangeability. This has to do with purely static, two-dimensional measurements on a very small space.

However, there are many situations in which the simultaneous monitoring of the vital parameters of a plurality of persons is desirable but cannot be carried out because of the above-mentioned limitations particularly with contact-based measurement methods, for example, in the case of performance diagnostics in sports centers or the monitoring of patients in hospitals, particularly in neonatal units. Added to this is the fact that patients could find the contact-based monitoring unpleasant.

SUMMARY OF THE INVENTION

Therefore, it is the object of the invention to develop a method and a device with which the non-contact determination of temporal color variations and intensity variations can be carried out simultaneously in a plurality of objects with subsequent analysis.

This object is met by a method described in the following for the non-contact determination of temporal color variations and intensity variations in objects—particularly also simultaneously in a plurality of objects—in a scene. The "scene" may be, for example, an enclosed space in a sports center or in a hospital but can also be a larger open area, for example, a soccer field or baseball field. The term "object" includes everything with which information can be provided about the state of the object by measuring temporal color variations and intensity variations, for example, light-emitting diodes or plants, but particularly persons who can also move freely within the scene. The objects are distributed within the scene, and the aim is to simultaneously measure the relevant color variations and intensity variations in determined regions of all of the objects and, based on the variations in color and intensity, to draw conclusions on specific parameters describing the state of the objects.

For this purpose, a stereoscopic overview map of the scene is initially generated in that a first monoscopic overview image of the scene from a predetermined first viewing direction and a second monoscopic overview image from a predetermined second viewing direction are detected in a first spectral range. The first viewing direction and second viewing direction differ from one another, their position relative to one another being known. The two monoscopic overview images are calculated to form the stereoscopic overview map from which the spatial positions of objects to be measured are ultimately determined. For this purpose, a first overview camera and a second overview camera are provided in the device according to the invention. The two cameras detect the same wavelength range or the same wavelength in each instance and are oriented to the scene in a fixed, predetermined first viewing direction and second viewing direction, respectively. The viewing directions preferably intersect at a point in or behind the scene so that viewing angles can be determined on the basis of this point and a reference axis. The information detected with the overview cameras is not dependent on the temporal color variations and intensity variations which are to be detected but rather serves to identify the position and possibly also the movement and movement direction of objects in the scene. The faster an object moves, the more overview images must be taken and the more overview maps must be calculated insofar as no approximate determination of the movement is possible.

In a second step, a two-dimensional detail image is detected in a second spectral range from a predetermined third viewing direction, the position of which relative to the first viewing direction and second viewing direction is known. The third viewing direction can differ from the first viewing direction and second viewing direction, which may possibly facilitate the calculation. But it can also correspond to one of the two viewing directions. For example, a camera can be used for both an overview image and a detail image. The capture of the two-dimensional detail image is preferably carried out simultaneous with the capture of the overview images so that the image contents illustrate an identical moment, or is carried out immediately before or after the capture of the overview images, for example, if the object does not move. A detail camera which is directed to the scene from the third viewing direction is used to capture the detail image. The two-dimensional detail image is then projected onto the stereoscopic overview map. Measurement surfaces are selected as regions of interest in the scene based on measurement criteria which are predetermined depending on parameters on which conclusions are to be drawn from the color variations and intensity variations. Like the calculation of the two monoscopic overview images to form the stereoscopic overview map, this is carried out in a computing unit formed for this purpose.

The position of all three viewing directions relative to one another is known; they preferably intersect at a point in the rear area of the scene or behind the scene. Since the position of the cameras relative to one another is known, a geometric calibration of the position of the detail camera in relation to the position of the overview camera can be carried out. Transformation matrices can then be determined on the basis of this calibration for a one-to-one transformation of the spatial image data of the stereoscopic image to the two-dimensional image data of the detail image, and vice versa. By projecting the two-dimensional detail image on the stereoscopic overview map, the position of measurement surfaces, also referred to as regions of interest (ROI), can be determined taking into account their position and possibly distortion in space. Optimal measurement regions, for example, skin locations in persons at which a particularly strong color variation is measurable because of good blood circulation, such as the forehead, neck or wrists, can be defined in this manner.

For capturing the detail image, it is advantageous to utilize a detail camera which has a very high resolution, particularly a resolution that is higher than that of the overview cameras, so that the measurement surfaces can be identified as accurately as possible. A somewhat lower resolution is generally sufficient to capture the overview image because the three-dimensional structures which can be represented by points and vectors, for example, as grids, generally have dimensions extending over a larger area of pixels. For example, overview cameras with a resolution of 832×632 pixels and detail cameras with a resolution of 1280×1024 pixels can be used. Good results can be achieved with these resolutions especially in enclosed spaces. The greater the detail a scene has, the higher the resolutions of the cameras which should be selected. However, overview cameras with higher resolution can be used to determine further parameters if required. If all of the cameras are identical and have identical resolutions, the evaluation may be simplified in certain circumstances.

After determining the measurement surfaces, light emitted from the measurement surfaces is detected in a spatially resolved and wavelength-resolved manner in a continuously captured series of measurement images in at least one measurement spectral range, which is predetermined depending on the measurement criteria, from a fourth viewing direction, the position of which in relation to the other three viewing directions is likewise known. A corresponding measurement camera is used for this purpose. The measurement camera or the area detector for registering the image data of this camera, respectively, advantageously has the same resolution as the detail camera, i.e., for example, 1280×1024 pixels, because a pixel-by-pixel association of the measurement surfaces is facilitated in this way. The detection is carried out in a spatially resolved manner, i.e., by means of an area detector, for example, a CMOS sensor. However, when at least two measurement spectral ranges are predetermined, the detection is also carried out in a wavelength-resolved manner, which means that the spectral ranges are detected independently from one another on the same area detector.

The data stream can be substantially reduced in that only image data in the measurement surfaces need be registered and subsequently evaluated. The frame rate, i.e., the quantity of images captured per second, depends on the type of objects to be measured and on the extent to which the objects move in the scene. For example, if static objects such as plants are observed from a static position over a longer period of time then, particularly in this instance, color changes are expected to take place over a longer period of time. In this case, it is sufficient, for example, to record images at intervals of several minutes, hours or days, in which case an overview map and a detail image are again also generally produced simultaneously in order to compensate for possible changes of position. On the other hand, with newborns a frame rate of at least 15 or 20 images per second will be selected so that a high pulse rate, i.e., the quantity of heartbeats per minute, can be correctly detected. A similar procedure is employed with athletes, in which case, generally, new overview maps and detail images must also be produced again and again between two series of measurement images because athletes generally move faster. The quantity of overview maps and detail images can be reduced when the objects are analyzed with respect to a movement between the recordings of two such datasets at different points in time and a displacement of the measurement surfaces can also be prognosticated in this way. Otherwise, overview maps and detail images are determined virtually continuously and measurement images of updated measurement surfaces are captured, the frame rate at which the measurement images are captured ultimately determining the frame rate of the system as a whole, since a higher frame rate for other cameras would only lead to a surplus of information which could not be utilized. All of the cameras are preferably capable of recording at the same maximum frame rate as the measurement camera.

The reliability of the measurements can be increased through the use of a stereoscopic overview map because the spatial position of the measured objects in the scene can be taken into account and appropriate corrections can be made in the image. Acquired measurement surfaces on the objects can be corrected for perspective distortions by projecting the two-dimensional detail image. Measurement data which are corrupted in this manner or measurement data with low reliability can also be excluded. In this way, the certainty of the measurement can be improved overall. Moreover, by means of the projection, the exact position of measured signals, i.e., the reflected colors, can be determined, which is advantageous when observing a group of moving objects.

The measurement is carried out only for wavelengths in at least one measurement spectral range which is predetermined depending on measurement criteria, that is, ultimately depending on the parameters on which conclusions are to be drawn. If there is only one individual wavelength that must be monitored, an appropriate filter which passes only light in the predetermined measurement spectral range can be arranged in the beam path in front of the measurement camera. Depending on the parameters on which conclusions are to be drawn, the predetermined measurement spectral range can be highly restrictive and pass only one wavelength, e.g., when only fluctuations in intensity are to be examined, or a broader wavelength range when color fluctuations are to be measured as well. For example, the measurement spectral range can be fixed at 420 nm to 450 nm when monitoring patients with jaundice because bilirubin, which is present in higher concentrations in this case, reflects in this range. Other exemplary measurement spectral ranges lie between 630 nm and 750 nm for the visible Hb band range (Hb hemoglobin) and between 800 nm and 940 nm for the near infrared range of the Hb band.

In the final step, the data detected on the measurement surfaces are analyzed in the measurement images with respect to temporal color variations and/or intensity variations. The results of the analysis are then displayed. This is generally carried out with the computing unit which is configured to analyze the temporal variation in the intensity and/or color of the light in the at least one measurement spectral range in the series of measurement images and to transmit the results to a corresponding display unit. The latter can be, for example, a monitor, a storage unit or—in case of critical values—a signal generator which alerts standby personnel.

For example, the pulse rate of an athlete or a newborn can be derived based on temporal color fluctuations in the near infrared wavelength range at a wavelength of approximately 830 nm in a range of +/−50 nm around this wavelength. Only the values of those measurement surfaces on exposed parts of the skin where the veins lie closer to the surface are analyzed.

However, it is advantageous if further relevant parameters can also be observed with the device and the method, for example, the oxygen content in the blood, for which purpose it is necessary to measure at a wavelength of approximately 650 nm. The relative oxygen saturation of the hemoglobin bound in the blood can be measured from the ratio of the measured intensities of the two wavelengths. To this end, the measurement image is detected in a spatially resolved and wavelength-resolved manner in at least two predetermined measurement spectral ranges.

A filter element which is formed as a nanooptical filter matrix is advantageously used so that a spatial resolution and wavelength resolution and a limitation to the measurement surfaces is achieved simultaneously for both wavelengths. This nanooptical filter matrix is mounted on a planar measurement sensor which detects the light emitted from the measurement surfaces in the measurement camera. For the purpose of detecting two measurement spectral ranges, the nanooptical filter matrix has two kinds of filter structure. First filter structures serve to filter a first measurement spectral range, and second filter structures serve to filter a second measurement spectral range. The first filter structures and second filter structures are preferably arranged in the nanooptical filter matrix in a checkerboard manner. In so doing, each of the filter structures covers a larger area of pixels. The operation of the nanooptical filter elements is based on the phenomenon of extraordinary optical transmission which occurs when electromagnetic radiation interacts with periodically arranged holes of nanoscopic dimensions. The spectral selectivity can be determined by means of the material, for example, gold or silicon, the array period or pitch of the holes and the diameter of the holes. If further measurement spectral ranges are to be analyzed, a suitably expanded checkerboard structure with three or more types of filter structure can be used.

In this way, the measurement of the selected measurement spectral ranges or wavelengths, respectively, is carried out so as to be spatially resolved in each instance and so as to be resolved according to wavelengths or spectral ranges in each instance, i.e., the measurement spectral ranges are detected without being influenced by one another, because, owing to the filter arrangement, the pixels arranged under the filter structures only detect either the one wavelength or the other or the one measurement spectral range or the other, i.e., actually measure only the intensity in one wavelength or in one wavelength range without being influenced by the former or the latter. In this way, the measurement signal is prepared already before the definitive evaluation by the computing unit, i.e., the utilized hardware. In contrast to reconstructions from superimposed measurements from two measurement spectral ranges in the RGB color space, no further calculations are needed and only the relevant color/wavelength is actually measured. This reduces the time required for processing the data by means of software, which reduces the latency of the measurement and increases real time capability. Further, parameters are also derived from the data more accurately when no algorithmic-numeric errors occur at all.

Further, the integration of nanooptical filter masks on an image sensor simplifies a large-scale production because the nanooptical filter matrices can be applied or structured in the same production step as the insertion of the camera sensor. Further, the integration of nanooptical filter elements increases mechanical robustness to shaking or vibrations of the measuring system and means compactness compared to conventional systems in which the filters are placed in front of the camera, as is also possible when only one wavelength is used. The nanooptical filter matrices can be applied to the camera sensor, for example, by means of bonding, that is, by using an adhesive which cures under UV radiation and which in the cured state has a refractive index similar to that of glass. The filter matrix can be produced separately on wafers, sawed out of the latter and glued to an existing chip. Another possibility consists in integrating the filter matrices directly in the manufacturing process for CMOS chips, for example, by means of electron beam lithography.

In order to increase the accuracy of the overview map, especially in enclosed spaces, a pattern is projected on the scene. In order to generate the stereoscopic overview map, a pattern is projected on the scene, this pattern being detected in the monoscopic overview images. A pattern projector which projects a pattern on the scene in the first spectral range is used to project the pattern. In this case, in a particularly preferable manner, the method of structured-light projection can be applied, i.e., the pattern is preferably striped without being limited to this arrangement. Other patterns which generate distinct differences in contrast, such as checkerboard patterns, can also be used. The first spectral range preferably comprises the near infrared range so that a projected pattern is not visible and is not irritating to humans or other living beings. For example, a so-called NIR gobo projector (NIR=near infrared, gobo=GOes Before Optics) can be used such as is described, for example, in the article "GOBO projection for 3D measurements at highest frame rates: a performance analysis" by S. Heist et al., published in *Light: Science & Applications* (2018) 7:71. Advantageously, the first spectral range and second spectral range do not overlap, so that the overview images and the detail image can be captured simultaneously without a mutual influence occurring in this case. Generally, the detail image is captured in the wavelength range visible to the human eye, whereas the overview images are captured in the infrared range, particularly the near infrared range, in order to avoid irritation. It is particularly advantageous for the capture of overview images, especially when using a pattern projector, if the scene is illuminated by an additional light source radiating light exclusively in the first spectral range, i.e., for example, in the near infrared range. This increases the accuracy of the overview measurement and, therefore, of the stereoscopic overview map.

As has already been explained, the viewing directions of all of the cameras relative to one another are known and the cameras are geometrically calibrated with respect to one another. For example, the first overview camera, second overview camera, detail camera and measurement camera are arranged in a circular arc, the first overview camera and second overview camera preferably being arranged at end points of the circular arc in order to realize the largest possible angular spacing, which is advantageous for the precision of the 3D measurement. All of the viewing directions can intersect at a point in the scene or behind it.

A substantially more compact arrangement is achieved when the first overview camera and second overview camera are arranged on a first circular arc and the detail camera and measurement camera are arranged on a second circular arc. The two circular arcs then intersect at an angle other than zero, preferably at an angle of 90°. The optional pattern projector can be placed in the center where the two circular arcs intersect. An arrangement of this kind can then be integrated in a housing as a constructional unit, the geometric calibration being carried out during assembly. This constructional unit can then be used flexibly and is transportable without auxiliary means.

The method and device can be used in particular for determining performance in sports. Medical applications consist in the monitoring of biosignals of patients in ambulatory or stationary environments. Vital parameters can also be measured without complications in intensive care medicine, especially in patients with unstable vital parameters, because no electrodes need to be applied. This is also advantageous particularly for monitoring especially lively patients such as newborns.

A further possible application consists in detecting stress in the workplace within the framework of health management operations. In psychological diagnostics, emotional and psychical stress values can be measured and evaluated in patients with emotional dysfunctions, such as occur, for example, after trauma or with congenital mental disorders. A common problem here is the inability of such patients to assess their own degree of stress level and the inability to communicate to a therapist or a doctor through gestures and facial expressions. With conditions such as autism, a further complicating factor consists in that contact-based vitals sensors cannot be attached without severely stressing the patient, if at all. A non-contact system allows therapists to be assisted in their work as well as to provide feedback and training for the patients. In this regard, however, pulse rate and oxygen content can only serve as indicators for a stress level and cannot be utilized by themselves for evaluation; further individual, subjective parameters should also be taken into account.

The method and the device according to the invention are also suitable for monitoring locations with large numbers of people, such as train stations or airports. By means of the simultaneous measurement of vital parameters and evaluation of stress values, faster assistance may be ensured in cases of medical emergency for the purpose of an early warning system on the one hand. For example, not only the pulse rate but also the pulse sequence over time, which reflects the heart rhythm, can be determined on the basis of the data recorded by means of the measurement camera. If irregularities occur in determined known patterns in this case, they may indicate, for example, a heart attack which is detected by the system. On the other hand, persons with elevated stress values as potential safety hazards can be specially monitored in order that safety measures may be initiated if necessary. In this instance, a high pulse rate could serve as a prequalification for persons who would then undergo a more exact behavioral analysis.

Other areas of use with suitable adaptation of the nanooptical filter elements for the corresponding wavelengths exist in biology, for example, in the measurement of characteristic wavelengths for the chlorophyll content—for example, at the florescence wavelengths of 435 nm and 675 nm for chlorophyll—in plants in order to determine their health. In this case, the overview images can be captured passively, i.e., without active illumination or other interaction with the object.

It will be understood that the features mentioned above and those yet to be explained below may be used not only in the stated combinations but also in other combinations or alone without departing from the scope of the present invention.

BRIEF DESCRIPTION OF THE DRAWINGS

The invention will be explained in more detail in the following with reference to the accompanying drawings which also disclose features key to the invention. The drawings show.

DETAILED DESCRIPTION OF THE DRAWINGS

Figure 1:
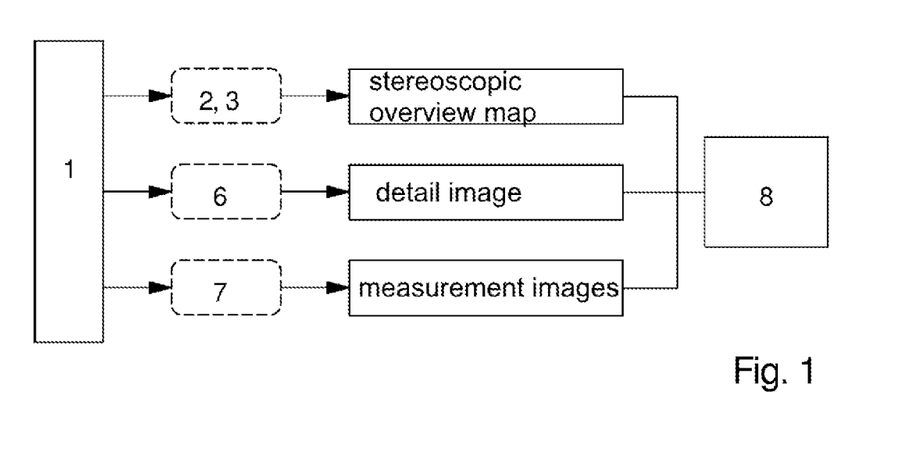
FIG. 1 the basic principle of a method for non-contact determination of temporal color variations in objects.
Figure 2A:
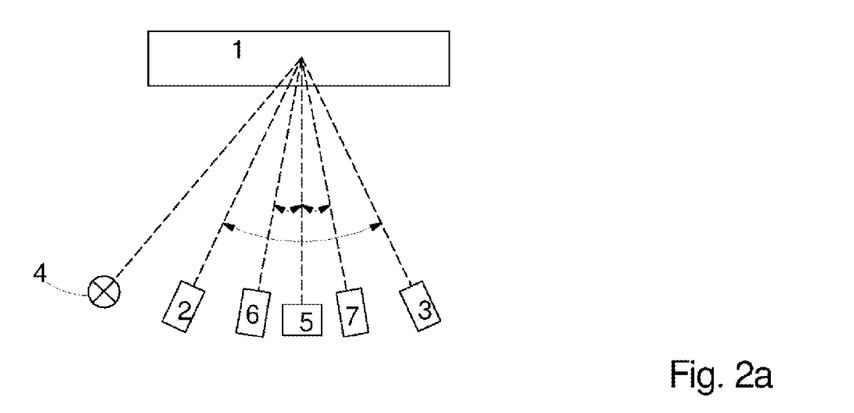
FIGS. 2a-b possible implementations of devices for carrying out the method.
Figure 2B:
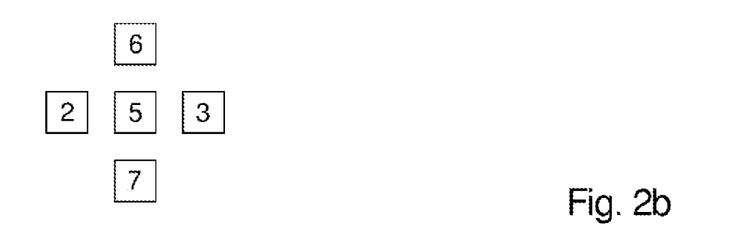

FIG. 1 shows the basic flow of a method for the non-contact determination of temporal color variations in a plurality of objects in a scene. A scene 1 is represented schematically on the left-hand side of FIG. 1. This can be, for example, a room in a fitness center or sports center, an area in a stadium, for example, in the area of the track, or stations or rooms in a hospital to name a few examples. Such scenes can also be forested areas or fields, plantations or parts thereof, etc. At least one object whose color variations are to be measured is located in the scene. For example, the object can be a plant or a plurality of plants, technical equipment emitting light, or people whose vital parameters are to be monitored, for example. The scene is captured by three different camera systems, each of which comprises one or more cameras, to allow the corresponding parameters to be monitored and evaluated. The first camera system comprises a first overview camera 2 which is directed to the scene 1 from a predetermined first viewing direction and a second overview camera which is directed to scene 1 from a predetermined second viewing direction. The two viewing directions differ from one another but are known so that a geometric calibration of the two cameras is possible. Exemplary setups are shown in FIGS. 2a and 2b.

Each of the two overview cameras 2, 3 captures a monoscopic overview image of the scene 1 in a first spectral range. The two monoscopic overview images are computed to form a stereoscopic overview map which also contains the depth information of the objects, i.e., their distance from the cameras or another reference point, so that the spatial position of all of the objects in the scene 1 which are to be measured, i.e., in all three spatial coordinates of a Cartesian system, is always known.

In order to improve illumination of the scene 1 and obtain a more accurate overview map, it can be advantageous to illuminate the scene with a separate light source 4 which emits light in the first spectral range. In order to prevent irritation of living objects and interactions with ambient light, a near infrared range comprising the wavelength range between approximately 780 nm and approximately 3000 nm is preferably selected as first spectral range. A light source 4 of this kind for separate illumination of the scene is shown in FIG. 2a in which all of the cameras are arranged on a circular arc. Increased accuracy can be achieved also or additionally if, in order to generate the stereoscopic overview map, a pattern is projected on the scene 1 which is detected in the monoscopic overview images. To this end, the arrangement comprises a pattern projector 5, shown in FIG. 2a, which projects a pattern, preferably a striped or checkerboard pattern, on the scene 1 in the first spectral range. A wavelength range which is not perceptible to the human eye, such as the near infrared range, is then particularly well suited as first spectral range especially for the projection of a pattern. It will be appreciated that the first spectral range is not limited exclusively to the near infrared range; wavelengths greater than 3000 nm can also be used, and wavelengths in the visible range or smaller wavelengths are also conceivable, for example, when the objects to be measured are not living objects.

The overview cameras 2 and 3 can have a high resolution but need not, since, in principle, only the position of the objects in space is to be determined in this case, these objects then being divided into individual surfaces, the dimensions of which are, however, generally greater than the dimensions of a pixel of a sensor used in a camera.

Simultaneously or immediately prior to or subsequent to the capture of the overview images, a two-dimensional detail image is detected in a second spectral range from a predetermined third viewing direction whose position in relation to the first viewing direction and second viewing direction is known. The third viewing direction can differ from the first two or can coincide with one of them. A detail camera 6 having the highest possible resolution is used for this purpose. The detail image is captured in a second spectral range which is preferably different from the first spectral range. The capture is preferably carried out in the spectral range that is visible to a human eye, i.e., in the spectral range between approximately 380 nm and approximately 780 nm. The two-dimensional detail image is projected on the stereoscopic overview map, which is carried out with the aid of a computing unit. Measurement surfaces are then selected as regions of interest in the scene based on measurement criteria depending on parameters on which conclusions are to be drawn from the color variations and intensity variations. In the case of athletes training on equipment provided specifically for this purpose or also in the case of newborns, these measurement surfaces are, for example, areas of exposed skin such as the neck, forehead or wrists which can be utilized for determining the vital parameters based on changes in color. Owing to the projection, interfering influences which could corrupt the measurement of color variations and intensity variations in the identified regions can also be taken into account and corrected. Examples of such interfering influences are the position of the measured objects relative to the camera, shadows or perspective distortions. By determining measurement surfaces which correspond to defined areas on a sensor of a camera, the expenditure for subsequent evaluation can be substantially reduced.

After the measurement surfaces have been selected, light which is emitted from the measurement surfaces is detected in a spatially resolved manner in at least one measurement spectral range, which is predetermined on the basis of measurement criteria, in a continuously captured series of measurement images from a fourth viewing direction whose position in relation to the other three viewing directions is known and which can accordingly be geometrically calibrated. A measurement camera 7 which is directed to the scene from the fourth viewing direction is utilized for this purpose.

In the series of measurement images, the color values and intensity values in the at least one predetermined measurement spectral range which are measured on the pixels of an area detector and which are associated with the respective measurement surfaces are analyzed with respect to the temporal variation of intensity and/or color of this light in the at least one measurement spectral range. A computing unit 8 which also processes the information from the other images is utilized for this purpose. The results of the analysis are then stored and/or displayed. If there are critical changes, for example, in the vital parameters of an athlete, appropriate alert signals can also be displayed or relayed to the appropriate person. This person may be the doctor on duty, for example, in case the vital parameters of patients are being monitored.

FIGS. 2a and 2b show two possible arrangements for the elements used in a device for the non-contact determination of temporal color variations and intensity variations in objects in a scene. In the setup shown in FIG. 2a, the first overview camera 2, the second overview camera 3, the detail camera 6 and the measurement camera 7 are arranged in a circular arc, and the viewing directions intersect at a point in the scene 1. A pattern projector 5 having a light source 4 which emits light in the first spectral range is optionally provided. The pattern projector can also be identical to one of the two overview cameras 1, 2 or integrated therein. A stereoscopic overview image can also be generated in this manner. The arrangement shown in FIG. 2a requires a relatively large amount of space but, since the distance between the two overview cameras 1 and 2 can be selected to be quite large, the accuracy is particularly high when using this arrangement, and it is therefore also particularly suitable for monitoring larger scenes in which overview maps are to be produced with high accuracy. More than two overview cameras may also be used in order to increase accuracy. It is also possible to couple a plurality of devices having measurement cameras directed to the scene from different viewing directions in order, for example, to capture a scene with many moving objects so that, as far as possible, objects are prevented from being completely hidden and therefore not accessible to measurement.

On the other hand, in the arrangement shown in FIG. 2b, the first overview camera 2 and the second overview camera 3 are arranged on a first circular arc. The detail camera 6 and the measurement camera 7 are arranged on a second circular arc, and the two circular arcs intersect at an angle of 90°. The optional pattern projector 5 is situated at the intersection of the circular arcs. In this instance also, all of the cameras are oriented such that their viewing directions intersect at a point in the scene 1 or behind the latter so that the cameras can be geometrically calibrated. The construction of the device shown in FIG. 2b is compact and therefore also transportable, for example, between different rooms of a sports facility or hospital, without much effort. The construction can be configured as a compact constructional unit of its own which optionally also contains a computing unit 8.

The quantity of measurement images captured per second for fixed measurement surfaces is related to the kind of color variations and intensity variations to be measured and the parameters related thereto. In case vital parameters are to be determined in athletes or patients, the quantity of images captured per second should be no less than 15 in order to obtain meaningful measurements which allow a reliable determination of the pulse rate. The chlorophyll content of plants, on the other hand, need not be monitored with such a high frame rate; in this case, substantially longer intervals of several hours to several days are sufficient. The rate of capture of overview images and detail images on the basis of which the measurement surfaces are determined depends on the characteristics of the scene. When monitoring the chlorophyll content of plants, the measurement surfaces can be recalibrated, for example, before every capture of a measurement image, by capturing overview images and a detail image. Conversely, when monitoring the vital functions of quickly moving athletes, the rate at which overview images and detail images are captured can always be in the range of a tenth of a second or less. On the other hand, when a patient is more or less at rest, it is generally sufficient to determine the measurement surfaces within the space of one to several minutes. It is also conceivable to take measurements only sporadically rather than continuously in patients, for example, once or twice within the space of several hours, in which case an overview map is determined and a detail image is captured before each measurement of the color variations and intensity variations.

The quantity of predetermined measurement spectral ranges in which color variations and/or intensity variations are to be measured and analyzed depends on the parameters on which conclusions are to be drawn. For monitoring light emitting diodes or plants, it may be sufficient to carry out the measurement in only one measurement spectral range. In general, this can be achieved with filters which are placed in front of an objective lens of the measurement camera, which allows a simple adjustment to various situations in which measurements are taken in only one measurement spectral range.

However, the spatially resolved and wavelength-resolved determination of the color variations and intensity variations is problematic when these changes are to be measured and analyzed in two or more measurement spectral ranges for each measurement surface. One example of this is the vital parameters of athletes or newborns, where temporal color fluctuations—what is meant here, as was mentioned in the introductory part, are intensity fluctuations of one or more colors which are expressed in a change in the overall color impression—can be utilized at a wavelength of about 750 nm, 830 nm or 940 nm to determine the pulse rate of the person in question. The oxygen saturation of hemoglobin bound in the blood can be determined with an additional measurement of intensity fluctuations at a wavelength of about 660 nm or, alternatively, also at about 750 nm, for which purpose the ratio of the measured intensities of both wavelengths must be taken, i.e., not only color fluctuations but also temporal intensity fluctuations must be determined at the wavelength of 830 nm. Accordingly, these values must be determined simultaneously for both wavelengths in order that the relative oxygen saturation of the hemoglobin can be measured. While the two wavelengths are about 150 nm apart, the two measurement spectral ranges which are to be measured overlap so that absolute color fluctuations in the wavelength can also be taken into account in the area between them. If an individual front lens filter is utilized as in the prior art to pass two wavelengths or wavelength ranges, the intensity of both wavelengths which are located relatively close to one another would be detected in every pixel in total, although the changes in intensity of each individual wavelength would not be derivable therefrom.

For this reason, when the measurement image is to be detected in at least two predetermined measurement spectral ranges, a nanooptical filter matrix is used and is arranged so as to make possible a spatially resolved and wavelength-resolved detection of the light emitted from the measurement surfaces. The measurement camera 7 generally has an area detector, for example, a CMOS sensor, as sensor. The nanooptical filter matrix is mounted directly on the measurement sensor to enable the spatially resolved and wavelength-resolved measurement.

The nanooptical filter matrix which can be utilized in the device for the non-contact determination of temporal fluctuations in intensity and color in objects of a scene 1 will be described in more detail in the following referring to FIGS. 3 to 5.

Figure 3A:
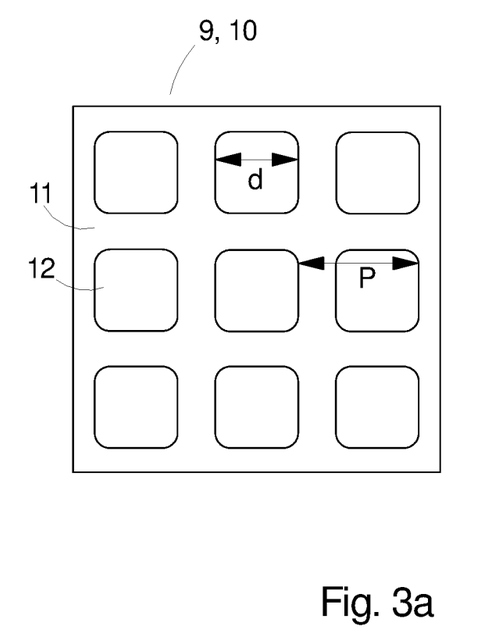
FIGS. 3a-b the basic construction of a nanooptical filter and cooperation with a CMOS sensor.

Shown on the left-hand side in FIG. 3a is the basic construction of a filter element which is formed as a nanooptical filter matrix 9 and which has first filter structures 10 serving to filter a first measurement spectral range. Holes 12 having a substantially square shape are arranged in a substrate material 11, for example, gold or silicon, although the holes can also have a round shape or can be slot-shaped. The holes 12 form an array or a matrix. The 3×3 structure shown here is also known as a nanohole array (NHA). The holes have a diameter d corresponding to the edge lengths, and like edges are spaced apart by a pitch P. Each of the holes 12 has a diameter of a few hundredths of a nanometer, and the size of the structure shown in FIG. 3a is approximately between 10 μm and 15 μm. Depending on the measurement situation, other sizes besides 3×3 structures are also possible for the individual matrix elements, for example, 4×4 or 5×5. However, 3×3 structures are optimal because, on the one hand, quite a large surface is available in each matrix element for measuring one of the spectral ranges and, on the other hand, the wavelength resolution is carried out with high accuracy in the spatial resolution.

The wavelength selectivity is influenced substantially by three parameters: the diameter or edge length d, respectively, of the holes, the spacing or pitch P of two holes 12 relative to one another, and the permittivity or electrical conductivity, respectively, of the utilized substrate material 11.

Figure 3B:
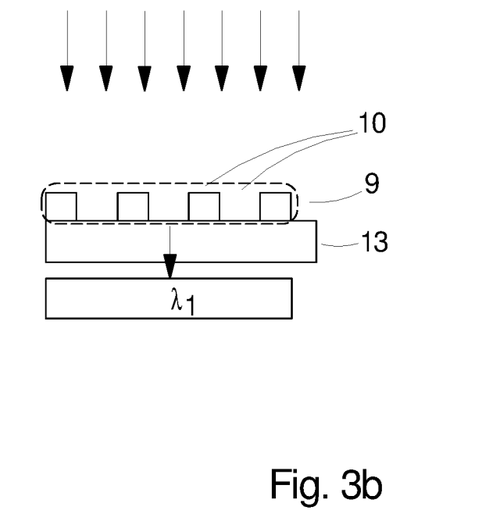

FIG. 3b shows the nanooptical filter matrix 9 arranged on a planar measurement sensor 13, for example, a CMOS chip. The nanooptical filter matrix 9 is mounted directly on the planar measurement sensor 13, for example, by bonding. While light of many wavelengths impinges on the nanooptical filter element, the filter is structured in such a way that it ideally only passes a wavelength $\lambda_1$ with a maximum bandwidth of 100 nm to 150 nm so that while, on the one hand, the color fluctuations in the wavelength can be registered, the passbands of two filter structures overlap as little as possible on the other hand. The nanooptical filter matrix 9 for a determined wavelength is transparent to this wavelength to the maximum extent, but the rest of the spectral range of a maximum of +/−75 nm around this wavelength is also passed, albeit only in a highly attenuated manner. However, the fluctuations in intensity are only relevant in a small range around the central peak wavelength at which the filter element has the highest sensitivity or highest transmission, respectively.

Figure 4:
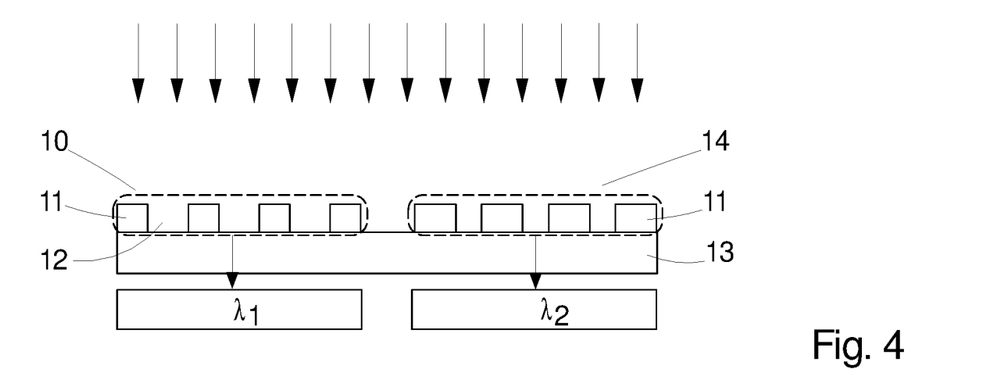
FIG. 4 a further embodiment of a nanooptical filter element.

FIG. 4 shows the implementation of a nanooptical filter matrix 9 which is transmissive to two peak wavelengths. The area on the left-hand side corresponds to the configuration shown in FIG. 3b. This first filter structure 10 is transmissive to a first measurement spectral range. A second filter structure 14 which has smaller holes than the first filter structure 10 is shown on the right-hand side, the pitch P of the first filter structure 10 being identical to that of the second filter structure 14. The second filter structure 14 is transmissive to a second measurement spectral region around a central wavelength or peak wavelength $\lambda_2$. While only wavelength $\lambda_1$ is passed on the left-hand side, the right-hand side is only transmissive to wavelength $\lambda_2$ or to the measurement spectral ranges defined around these central wavelengths. In this way, light can be detected such that it is simultaneously spatially resolved and wavelength-resolved; by the latter is meant the spectral resolution according to measurement spectral ranges.

Figure 5:
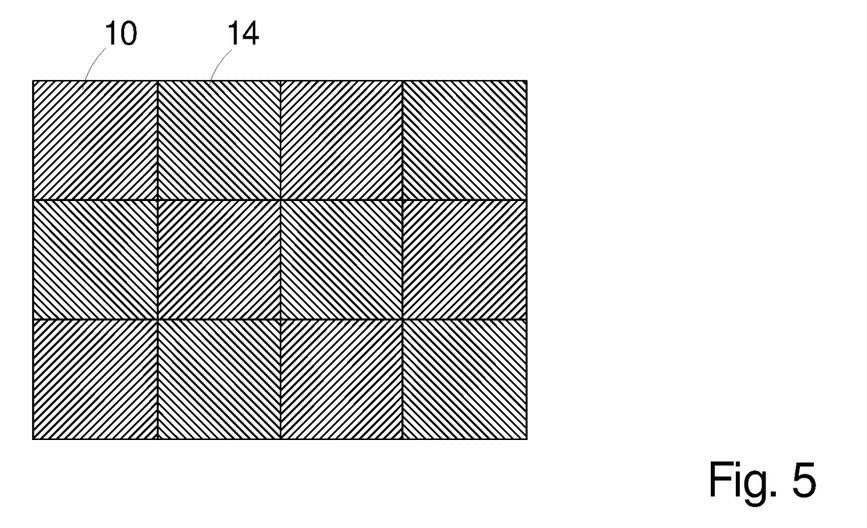
FIG. 5 a nanooptical filter element for two wavelengths.

A spatially resolved and wavelength-resolved detection is possible over the entire measurement sensor 13 in that the first and second filter structures 10, 14 are arranged in a checkerboard manner as is shown in FIG. 5, each filter structure corresponding to a nanooptical filter matrix 9, and this checkerboard structure is arranged on and connected to the planar measurement sensor 13. Each of the first filter structures 10 and second filter structures 14 covers an area of one pixel or a small quantity of a plurality of pixels so that it is ensured that a plurality of the first filter structures 10 and second filter structures 14 are associated with each measurement surface. In the case of monochromatic pixels, which is possible because of the color filtering used, one of the filter structures, i.e., a "hole", covers a pixel or an integral multiple thereof so that it is ensured that the two wavelength ranges are not detected on one pixel. In color sensors, four subpixels are generally combined to form one pixel, and the same then applies for these pixels as for the monochromatic pixels.

Figure 6:
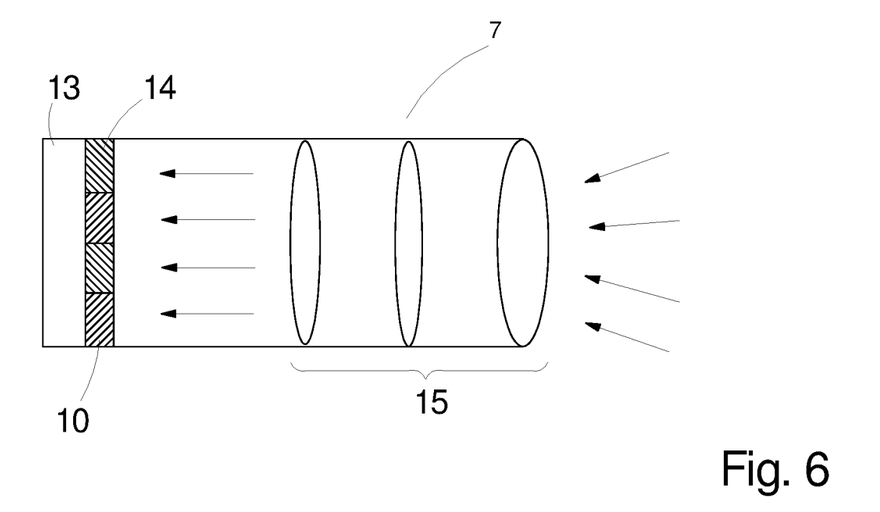
FIG. 6 the arrangement of a nanooptical filter element in a camera.

FIG. 6 shows the installation in the camera by way of example. In this case, incident light impinges on a lens system 15 of a measurement camera 7. The relevant wavelengths from direction of the measurement surfaces are now detected in a spatially resolved and wavelength-resolved manner via the nanooptical filter matrix 9 comprising the first filter structures 10 and second filter structures 14. Since the separation of the corresponding wavelengths is already carried out in this case by means of hardware, less time is required for processing data by means of software, which results in increased real time capability and reduced latency of the measurements. The production process is also simplified with respect to a large-scale production because the nanooptics can be applied or structured in the same production step for insertion of the camera sensor. The integration of the nanooptical filter elements on the sensor also augments the robustness to shaking or vibrations. Further, the construction can be configured somewhat more compactly because a filter in front of the measurement camera is no longer needed.

The use of a camera system such as is shown with its individual components in FIG. 2b by way of example is particularly suitable for monitoring persons in enclosed spaces. For example, preterm infants or newborns can be monitored in a corresponding neonatal unit, or athletes can be monitored in a training room. The camera system may be installed as a stationary measuring instrument. For example, it can be oriented such that it is directed to the persons to be monitored from the ceiling or wall or, in the case of newborns, to the bed or changing table, for example. The camera system initially detects the body of the person with the two overview cameras 2, 3. Areas of exposed skin which correspond to the measurement surfaces can be marked with the detail image which is captured simultaneously by the detail camera 6 and which is projected on the overview map generated from the overview images. Only the measurement surfaces are considered in the subsequent analysis. The measurement camera 7 and the nanooptical filter structures are configured to pass wavelengths around a central wavelength of 830 nm and 660 nm, the first filter structures 10 being transparent to one wavelength and the second filter structures being transparent to the other wavelength. The quantity of heart beats per minute which determines the heart rate can be directly determined from the temporal color fluctuations—in medical applications, in this specific case, this actually has to do with intensity fluctuations in a wavelength—in the near infrared range at the wavelength of 830 nm, which color fluctuations can be derived from the temporally consecutive recordings of the measurement surfaces. The spectral range around a wavelength of approximately 660 nm of the measurement surfaces is detected by means of the second filter structures 14. The relative oxygen saturation of the hemoglobin bound in the blood can be determined from the ratio of the measured intensities of the two wavelengths. In this case, the maximum values of the intensity distributions are compared. These values can be referenced with the help of lookup tables and converted into quantitative absolute values.

Figure 7:
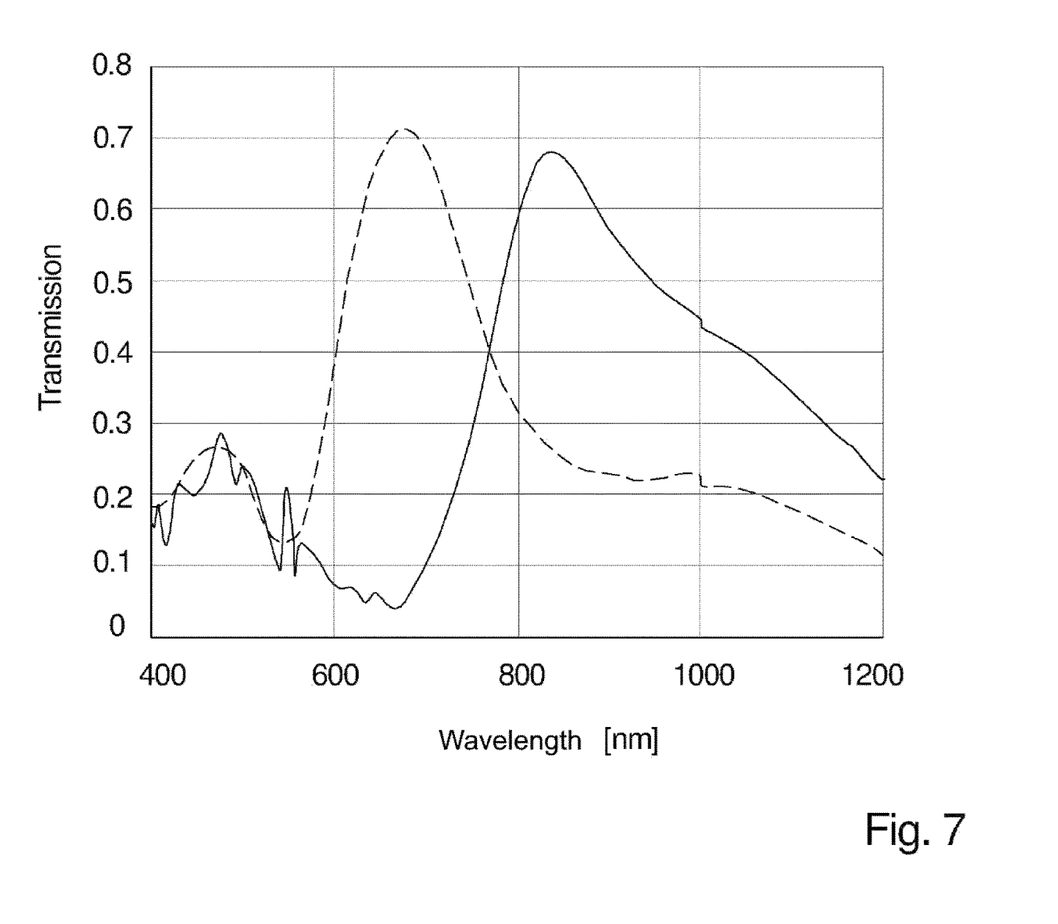
FIG. 7 the transmission characteristics of such a nanooptical element for two exemplary wavelength ranges.

An example for a measurement of the two wavelengths is shown in FIG. 7 for a given point in time of the recording of the series of measurement images. The solid line corresponds to the spectral range passed by the first filter structures 10 with a transmission maximum of approximately 850 nm in this instance. The dashed line corresponds to the spectrum passed by the second filter structures 14 with a maximum of about 660 nm.

In the case of persons at rest, for example, newborns, the respiratory rate and the respiratory volume can be determined additionally when the overview images are also captured with high resolution. These values can be derived from the three-dimensional contraction and expansion of the rib cage. For this purpose, overview images must be taken in a faster sequence at a rate corresponding at least to twice the respiratory rate.

Important vital parameters can be monitored in persons by means of the device described in the preceding and the method implemented therein, as well as other parameters to be monitored in a non-contact manner in plants, technological objects which emit light, etc. Compared to conventional methods, this results, for one, in reduced effort for the persons to be monitored as well as for the persons carrying out the monitoring compared to contact-based monitoring and, further, makes it possible to simultaneously monitor a plurality of persons, for example, with respect to vital parameters. Beyond this, a plurality of important vital parameters can be evaluated simultaneously with high accuracy.

REFERENCE CHARACTERS 1 scene
2 first overview camera
3 second overview camera
4 light source
5 pattern projector
6 detail camera
7 measurement camera
8 computing unit
9 nanooptical filter matrix
10 first filter structure
11 substrate material
12 hole
13 planar measurement sensor
14 second filter structure
15 lens system
d diameter
P pitch

The invention claimed is:

1. A method for non-contact determination of temporal color variations and/or intensity variations in objects in a scene, comprising:
   detecting a first monoscopic overview image of the scene in a first spectral range from a first predetermined viewing direction,
   detecting a second monoscopic overview image in the first spectral range from a second predetermined viewing direction differing from the first viewing direction,
   calculating the monoscopic overview images to form a stereoscopic overview map,
   determining spatial positions of objects to be measured from the stereoscopic overview map,
   detecting a two-dimensional detail image in a second spectral range from a predetermined third viewing direction, a position of which in relation to the first viewing direction and the second viewing direction is known,
   projecting the two-dimensional detail image on the stereoscopic overview map, and
   Selecting measurement surfaces as regions of interest in the scene based on measurement criteria depending on parameters on which conclusions are to be drawn from the color variations and/or intensity variations,
   detecting light emitted from the measurement surfaces in at least one measurement spectral range, which is predetermined as a function of the measurement criteria, from a fourth viewing direction, a position of which in relation to the first, second and third viewing directions is known, in a spatially resolved and wavelength-resolved manner in a continuously captured series of measurement images,
   analyzing the measurement surfaces in the measurement images with respect to temporal variation of the intensity and/or color of the light in the at least one measurement spectral range, and
   displaying the results of the analysis.

2. The method according to claim 1, wherein at least two overview maps and detail images are detected at different times and the objects are analyzed with respect to a movement, and, in case the objects move, overview maps and detail images are continuously determined and measurement images of updated measurement surfaces are recorded.

3. The method according to claim 1, wherein the measurement image is detected in a spatially resolved and wavelength-resolved manner in at least two predetermined measurement spectral ranges using nanooptical filter element.

4. The method according to claim 1, wherein a pattern is projected on the scene in order to generate the stereoscopic overview map, which pattern is detected in the monoscopic overview images, wherein light of wavelengths outside of the second spectral range for the recording of the detail image is used for the projection and detection of the pattern.

5. The method according claim 1, wherein light in the infrared wavelength range is used to generate the overview map and light in the visible wavelength range is used to generate the detail image.

6. A device for non-contact determination of temporal color variations and/or intensity variations in objects in a scene, comprising:
- a first overview camera which is directed to the scene from a predetermined first viewing direction and which captures a first monoscopic overview image of the scene in a first spectral range,
- a second overview camera which is directed to the scene from a predetermined second viewing direction and which captures a second monoscopic overview image of the scene in the first spectral range, wherein the first viewing direction and the second viewing direction differ from one another,
- a detail camera which is directed to the scene from a predetermined third viewing direction, a position of which in relation to the first viewing direction and second viewing direction is known, and captures a two-dimensional detail image,
- a computer configured to calculate the first monoscopic overview image and the second monoscopic overview image to form a stereoscopic overview map and, based on the overview map, determine a spatial position of objects to be measured, project the two-dimensional detail image on the overview map and, based on the measurement criteria, select the measurement surfaces on the objects as regions of interest in the scene depending on parameters on which conclusions are to be drawn from the color variations and/or intensity variations, and
- a measurement camera which is directed to the scene from a predetermined fourth viewing direction, a position of which in relation to the first, second and third viewing directions is known, and light emitted from the measurement surfaces is detected in at least one measurement spectral range, which is predetermined as a function of the measurement criteria, in a spatially-resolved and wavelength-resolved manner in a continuous series of measurement images,
- wherein the computer is further configured to analyze the temporal variation in the intensity and/or color of the light in the at least one measurement spectral range in the series of measurement images and to transmit the results to a display unit.

7. The device according to claim 6, wherein the first overview camera and the second overview camera, the detail camera and the measurement camera are arranged in a circular arc.

8. The device according to claim 6, wherein the first overview camera and second overview camera are arranged on a first circular arc, and the detail camera and measurement camera are arranged on a second circular arc, these circular arcs intersecting at an angle other than 0°.

9. The device according to claim 6, wherein the first spectral range lies outside of the spectral range that is visible to a human eye.

10. The device according to claim 6, wherein the scene is illuminated by a light source which emits light predominantly or exclusively in the first spectral range.

11. The device according to claim 6, further comprising a pattern projector which projects a pattern on the scene in the first spectral range.

12. The device according to claim 6, wherein a planar measurement sensor for detecting the light emitted by the measurement surfaces is arranged in the measurement camera, and a filter element which is transparent to light of the at least one measurement spectral range is mounted on the planar measurement sensor, and wherein the filter element is formed as a nanooptical filter matrix.

13. The device according to claim 12, wherein the measurement camera is formed to detect two predetermined measurement spectral ranges, for which purpose the nanooptical filter matrix has first filter structures for filtering a first measurement spectral range and second filter structures for filtering a second measurement spectral range.

14. The device according to claim 7, wherein the first overview camera and the second overview camera are arranged at end points of the circular arc.

15. The device according to claim 8, wherein the angle other than 0° is an angle of 90°.

16. The device according to claim 9, wherein the first spectral range is in the infrared range.

17. The device according to claim 16, wherein the first spectral range is in the near-infrared range.

18. The device according to claim 11, wherein the pattern is a striped pattern.

19. The device according to claim 13, wherein the first filter structures and the second filter structures are arranged in the nanooptical filter matrix in a checkerboard manner.

* * * * *